United States Patent
Day

(10) Patent No.: US 6,479,038 B1
(45) Date of Patent: Nov. 12, 2002

(54) CLEAR DENTIFRICE GELS

(75) Inventor: Trevor Neil Day, Windsor (GB)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/719,269

(22) PCT Filed: Jun. 11, 1999

(86) PCT No.: PCT/US99/13011

§ 371 (c)(1),
(2), (4) Date: Dec. 8, 2000

(87) PCT Pub. No.: WO99/63960

PCT Pub. Date: Dec. 16, 1999

(30) Foreign Application Priority Data

Jun. 12, 1998 (GB) ............................................. 9812820

(51) Int. Cl.$^7$ .............................. A61K 7/16; A61K 7/18
(52) U.S. Cl. .............................. 424/57; 424/49; 424/52
(58) Field of Search ..................................... 424/49–58

(56) References Cited

U.S. PATENT DOCUMENTS

| 3,927,201 A | * 12/1975 | Baines et al. ................. 424/54 |
| 3,927,202 A | * 12/1975 | Harvey et al. ................. 426/57 |
| 4,272,509 A | * 6/1981 | Wason ........................ 424/49 |
| 4,999,184 A | 3/1991 | Parran, Jr. et al. ............ 424/52 |
| 5,252,313 A | * 10/1993 | Collins et al. ................. 424/49 |
| 5,354,550 A | * 10/1994 | Collins et al. ................. 424/49 |
| 5,582,816 A | * 12/1996 | Mandanas et al. ............. 424/49 |
| 5,628,985 A | * 5/1997 | Stiller et al. ................... 424/49 |

FOREIGN PATENT DOCUMENTS

| EP | 0 549 287 | 6/1993 | ............ A61K/7/16 |
| WO | WO 96/38123 | 12/1996 | ............ A61K/7/16 |

* cited by examiner

Primary Examiner—Shep K. Rose
(74) Attorney, Agent, or Firm—Emelyn L. Hiland; Karen F. Clark; Betty J. Zea

(57) ABSTRACT

According to the present invention there is provided a visually clear, dentifrice gel comprising; a) sufficient tetrasodium pyrophosphate to provide from 0.2% to 5% pyrophosphate anion; b) a silica dental abrasive having a refractive index of from 1.445 to 1.47; c) from 0.7% to 3% sodium alkyl sulphate; and d) an aqueous liquid carrier. The gel has excellent clarity, high anticalculus efficiency and good foaming. According to a further aspect of the invention there is provided a process for making a clear dentifrice gel comprising the step of adding anhydrous tetrasodium pyrophosphate to an aqueous carrier, the gel comprising: a) a silica dental abrasive having a refractive index of from 1.445 to 1.47; and b) an aqueous liquid carrier comprising less than 27% total water. The use of anhydrous tetrasodium pyrophosphate allows greater formulation flexibility at the processing stage by freeing up water for the dissolution and/or hydration of other dentifrice components.

6 Claims, No Drawings

CLEAR DENTIFRICE GELS

FIELD OF THE INVENTION

The present invention relates to clear dentifrice gels comprising a tetrasodium pyrophosphate anticalculus agent.

BACKGROUND OF THE INVENTION

Dentifrices which are visually clear are appealing to consumers. Such products must also provide a functional benefit however. There are many dentifrice compositions which contain active agents to prevent the beginnings of gum disease, calculus build-up and cavities. The active agents of a dentifrice are those agents which inhibit the formation of calculus and prevent the accumulation of plaque bacteria and other micro-organisms which are responsible for halitosis, plaque, caries and gum diseases such as periodontitis and gingivitis.

Dental calculus, or tartar as it is sometimes called, is a deposit which forms on the surfaces of the teeth at the gingival margin. Supragingival calculus appears principally in the areas near the orifices of the salivary ducts; e.g., on the lingual surfaces of the lower anterior teeth and on the buccal surfaces of the upper first and second molars, and on the distal surfaces of the posterior molars.

Mature calculus consists of an inorganic portion which is largely calcium phosphate arranged in a hydroxyapatite crystal lattice structure similar to bone, enamel and dentine. An organic portion is also present and consists of desquamated epithelial cells, leukocytes, salivary sediment, food debris and various types of micro-organisms. As the mature calculus develops, it becomes visibly white or yellowish in colour unless stained or discoloured by some extraneous agent. This is undesirable from an aesthetic standpoint.

Mechanical removal of calculus periodically by the dentist is routine dental office procedure. A variety of chemical and biological agents have also been suggested to retard calculus formation or to remove calculus after it is formed. Pyrophosphate salts are chemical agents knows to have the ability to retard calculus formation as described, for example, in U.S. Pat. No. 4,999,184, to Parran, Jr. et al., issued Mar. 12, 1991, the disclosure of which is incorporated herein by reference in its entirety.

Tetrasodium pyrophosphate is one of the most useful pyrophosphate salts in this respect. However, due to its limited solubility it can be difficult to incorporate at highly effective levels. This is particularly true at high pH where the pyrophosphate anion is most effective as an anticalculus agent, or when the available water in the dentifrice is restricted. Furthermore, its use at substantial levels can introduce further formulation difficulties because of the 'salt' content that it introduces into the aqueous phase, potentially leading to salting out of surfactant and resulting cloudiness in an otherwise clear gel.

It is customary for a dentifrice product to incorporate a dental abrasive, for the purpose of cleaning and polishing the teeth. Silica dental abrasives, of various types are particularly useful because of their unique benefits of exceptional dental cleaning and polishing performance without unduly abrading tooth enamel or dentine.

The broad principles of formulating a clear gel are well known; the refractive indices of the various dentifrice components—typically a liquid vehicle comprising water and various humectants—and insoluble components such as the abrasive must be matched. This can present considerable problems however, unless compromises are to be made on the functionality of the dentifrice. Accordingly, there is a substantial amount of prior art in relation to the formulation of clear dentifrice gels.

Illustrative of the art is WO 96/38123 which relates to a clear gel dentifrice comprising a silica of refractive index (RI) 1.44 and a selected liquid vehicle. The document discloses water soluble polyphosphate salts, at levels of from 0.1 to 7%, as optional components and the examples include 2% tetrasodium pyrophosphate as an anticalculus component, along with 1.2% sodium lauryl sulphate surfactant. Nevertheless, the water content of the dentifrice compositions of WO96/38123, from 27% up to 36%, is relatively high and there is no teaching of how to include moderate to high levels of tetrasodium pyrophosphate under the more demanding conditions of lower water content or high pH where a substantial portion of the tetrasodium pyrophosphate is likely to remain undissolved and where salting out effects are more critical.

U.S. Pat. No. 3,927,202 describes a clear gel dentifrice comprising an alkali metal phosphate salt, which can be tetrasodium pyrophosphate decahydrate, of RI 1.435 to 1.465 as a polishing agent, and a liquid humectant vehicle comprising no more free water than would dissolve about 30% by weight of the polishing agent at 40° C. The gels of U.S. Pat. No. 3,927,202 optionally comprise 0.5–20% silica abrasives of RI 1.44 to 1.47. Although the document discloses a broad range of surfactants the examples all incorporate sodium N-lauroyl sarcosinate which is a relatively poor foamer. In practice, it has been found that substitution of sodium alkyl sulphate into the tetrasodium pyrophosphate decahydrate examples of U.S. Pat. No. 3,927,202 gives opaque compositions.

It has now surprisingly been found that a dentifrice gel of excellent clarity, high anticalculus efficacy and good foaming can be formulated by selecting a silica dental abrasive with a RI matched to that of tetrasodium pyrophosphate decahydrate (1.45–1.46) and by incorporating sodium alkyl sulphate as a surfactant.

It has further surprisingly been found that a dentifrice gel of excellent clarity and with high anticalculus efficacy can be formulated by selecting a silica dental abrasive with a RI matched to that of tetrasodium pyrophosphate decahydrate (1.45–1.46), even when the anhydrous form of tetrasodium pyrophosphate, which has a RI of 1.425, is utilised. This is believed to be due to in situ hydration of the anhydrous form to the decahydrate. The use of anhydrous tetrasodium pyrophosphate allows greater formulation flexibility at the processing stage by freeing up water for the dissolution and/or hydration of other dentifrice components.

SUMMARY OF THE INVENTION

According to the present invention there is provided a visually clear, dentifrice gel comprising:
a) sufficient tetrasodium pyrophosphate to provide from 0.2% to 5% pyrophosphate anion;
b) a silica dental abrasive having a refractive index of from 1.445 to 1.47;
c) from 0.7% to 3% sodium alkyl sulphate; and
d) an aqueous liquid carrier.

The gel has excellent clarity, high anticalculus efficacy and good foaming.

According to a further aspect of the invention there is provided a process for making a visually clear, dentifrice gel comprising the step of adding anhydrous tetrasodium pyrophosphate to an aqueous carrier, the gel comprising:

a) a silica dental abrasive having a refractive index of from 1.445 to 1.47; and b) an aqueous liquid carrier comprising less than 27% total water.

The use of anhydrous tetrasodium pyrophosphate allows greater formulation flexibility at the processing stage by freeing up water for the dissolution and/or hydration of other dentifrice components.

All percentages and ratios used herein are by weight of the total composition unless otherwise specified. All measurements are made at 25° C., unless otherwise specified.

DETAILED DESCRIPTION OF THE INVENTION

The term "gel", as used herein, refers to a product having a consistency sufficient to maintain the undissolved particulates in stable suspension. Included within this scope are stiff gels and so-called "liquid" dentifrices, such as those described in U.S. Pat. No. 5,695,746. The clear gel dentifrice can be a single homogeneous product, but it can also form part of a multiphase product such as a deep or surface striped dentifrice or multiphase product stored in a dual compartment, wherein the entire product comprises other physically distinct components which may not be clear or otherwise conform to the clear gel compositions of the invention. The clear gel may also have dispersed within it small amounts of visible particulates e.g. coloured speckle, provided that the inherent clarity of the gel is apparent.

In terms of clarity, the liquid carrier of the dentifrice preferably has a clarity index of less than about 500 nephetometric turbidity units (NTU), preferably less than about 300 NTU, even more preferably less than about 200 NTU, clarity being measured at 20° C. using a Orbico-Hellige Series 965 Turbidity Meter calibrated over the range 0 to 999 NTU.

The present compositions comprise essential components, as well as optional components. The essential and optional components of the gel compositions of the present invention are described in the following paragraphs.

Tetrasodium Pyrophosphate

The gel compositions of the present invention include tetrasodium pyrophosphate. Tetrasodium pyrophosphate is commercially available as both a decahydrate salt and in anhydrous form. For the purposes of the present invention the anhydrous form is highly preferred. On a weight basis, the decahydrate form includes about 40% water of crystallisation. Depending upon the crystalline form, the refractive index (RI) of the decahydrate is in the range from 1.45 to 1.46. The refractive index of the anhydrous form is about 1.425. It has been found that, provided there is sufficient available water in the formulation, the anhydrous form will hydrate within the dentifrice to form the decahydrate. Thus, even though the anhydrous form RI is substantially below that of the preferred silica, its RI becomes matched on formulation into the dentifrice. Until the anhydrous pyrophosphate is added however, the water of hydration may be used for the purpose of dissolving other water soluble dentifrice components or for improving the processing characteristics of the gel, such as by decreasing the viscosity.

Tetrasodium pyrophosphate is only moderately water soluble. At low available water levels therefore it remains substantially undissolved (50% or less of the salt dissolving in the neat dentifrice). By keeping the water level low this can be turned to advantage since pyrophosphate is susceptible to hydrolysis, particularly in the presence of fluoride ion. Whilst the tetrasodium pyrophosphate is in crystalline form, hydrolysis is substantially inhibited. This is particularly true at pH 8 and above where the pyrophosphate anion is most effective as an anticalculus agent.

In general, sufficient tetrasodium pyrophosphate is used to provide at least about 0.2% preferably at least about 1%, more preferably at least about 1.5% pyrophosphate anion. Typically effective anticalculus levels need be no more than about 5%. Higher levels can give rise to irritancy. Preferred levels of pyrophosphate anion are less than about 4% preferably less than about 3%.

Other pyrophosphate salts, such as dialkali metal pyrophosphate salts, especially disodium dihydrogen pyrophosphate and tetrapotassium pyrophosphate can additionally be incorporated in the gel compositions of the present invention provided they do not interfere with the clarity of the gel. Tetrapotassium pyrophosphate is more soluble than the tetrasodium salt and the potassium ions it provides can lead to the precipitation of potassium alkyl sulphate, it is therefore only employed in moderate levels, if at all.

Optional agents to be used in combination with the pyrophosphate salt include such materials known to be effective in reducing calcium phosphate mineral deposition related to calculus formation. Agents included are synthetic anionic polymers [including polyacrylates and copolymers of maleic anhydride or acid and methyl vinyl ether (e.g., Gantrez), as described, for example, in U.S. Pat. No. 4,627,977, to Gaffar et al., the disclosure of which is incorporated herein by reference in its entirety; as well as, e.g., polyamino propoane sulfonic acid (AMPS)], zinc citrate trihydrate, diphosphonates (e.g., EHDP; AHP), polypeptides (such as polyaspartic and polyglutamic acids), and mixtures thereof.

Polyphosphates can additionally be incorporated in the gel compositions of the present invention provided they do not interfere with the clarity of the gel. Useful polyphosphates consist of three or more phosphate molecules arranged primarily in a linear or cyclical configuration, preferably linear. Examples include sodium tripolyphosphate, tetrapolyphosphate and hexametaphosphate, among others.

Silica Abrasive

The gel compositions of the present invention include a silica dental abrasive having a refractive index of from 1.445 to 1.471. Silica dental abrasives of various types are preferred because of their unique benefits of exceptional dental cleaning and polishing performance without unduly abrading tooth enamel or dentine. The silica abrasive materials herein generally have an average particle size ranging between about 0.1 to about 30 microns, and preferably from about 5 to about 15 microns. The abrasive is preferably a precipitated silica. Suitable silicas commercially available silicas, of varying abrasivity, include Sorbosil® AC30 and AC39 from Crosfield, Syloblanc® 81 from Grace. Preferred herein is the silica carrying the designation "Zeodent® 115" from J. M. Huber Corporation which has high optical transparency at RI 1.45. The silica abrasive in the gel compositions described herein is generally present at a level of from about 1% upwards, preferably from about 10%, more preferably from about 15%. Levels up to 50%, preferably up to 30% can be employed. Mixtures of suitable silicas can of course also be employed, such as employing a mixture of two silicas of very similar RI but differing substantially in abrasivity or particle size.

The amount and type of silica abrasive or mixture of silica abrasives is generally chosen such that the gel of the present invention has a Radioactive Dentin Abrasion ("RDA") from 50 to 200. The RDA values are determined according to the method set forth by Hefferen, "Journal of Dental Research", July–August 1976, pp. 563–573, and described in the Wason U.S. Pat. Nos. 4,340,583, 4,420,312 and 4,421,527, which publication and patents are incorporated herein by reference.

The gels of the present invention can also comprise a thickening silica. Thickening silicas generally have a sub micron particle size which does not give rise to light scattering or otherwise interfere with the clarity of the gel. Suitable silicas for the present invention are marketed under the trade names Aerosil® 200 by Degussa and Cab-O-Sil® M-5 available from Cabot. A preferred thickening silica is marketed under the name Tixosil® 43 by Rhône-Poulenc. Thickening silicas are usefully employed at levels of from about 1 up to about 7%, preferably from 2% to 5%.

Anionic Surfactants

The gels of the present invention typically further comprises an anionic surfactant to enhance cleaning and foaming. In a first aspect of the present invention the gels comprise a sodium alkyl sulphate as an essential component. Sodium alkyl sulphate is preferred for its good overall acceptance profile and its high foaming characteristics. By "alkyl sulphate" is meant herein the water-soluble salts of alkyl sulphates having from 8 to 20 carbon atoms in the alkyl radical. Preferably dentifrice of the present invention comprise the anionic surfactant sodium lauryl sulphate. Further anionic surfactants useful herein include the potassium alkyl sulphates having from 8 to 20 carbon atoms in the alkyl radical (e.g., sodium alkyl sulphate), sulphoacetates, alkyl glyceryl sulphonates and the sarcosinates. Non-limiting examples of the anionic surfactants of this type which are suitable for the present invention are sodium decyl sulphate, sodium lauryl sulphosuccinate, sodium lauryl sulphate and sodium lauroyl sarcosinate. Anionic surfactants can be used at levels as low as about 0.1%. Highly preferred levels of anionic surfactant, and especially of sodium alkyl sulphate, are from about 0.7 to about 3%, preferably from about 1% to about 2%.

Aqueous Carrier

The gel compositions of the present invention include, as an essential component, an aqueous liquid carrier. The carrier comprises water and one or more humectants to match the refractive index of the carrier to that of the silica and pyrophosphate. Water used in the preparation of these compositions should preferably be of low ion content and free of organic impurities. The "total water content" of the composition, as used herein, includes the free water which is added plus the water which is introduced with other materials, such as with sorbitol, silica, colour solutions, surfactant solutions, or water of crystallisation of materials such as tetrasodium pyrophosphate decahydrate. The total water content of the gels of present invention is suitably less than about 30%, more preferably from less than about 27%, and especially less than about 25%. The gels preferably also comprise more than about 15%, more preferably more than about 20% total water.

Humectants are highly desirable components of the liquid carrier. The humectant serves to keep dentifrice compositions from hardening upon exposure to air and certain humectants can also impart desirable sweetness of flavour to dentifrice compositions. Furthermore, the humectants are normally essential for balancing the refractive index of the aqueous liquid carrier since water has a relatively low RI of 1.33. Suitable humectants for use in the invention include xylitol, glycerin, sorbitol (typically used as a 70% aqueous solution), polyethylene glycols of MW 1500 or less, propylene glycol and combination thereof The most preferred humectant is sorbitol. If sorbitol is used then, for best clarity of the gel, it is also preferred to employ a secondary humectant selected from glycerin, propylene glycol, polyethylene glycols of MW less than 1500 and mixtures thereof The total amount of humectant generally comprises from about 10% to about 60%, preferably from about 20% to about 55%, and more preferably from about 25% to about 50% on a 100% active basis. Xylitol may provide a therapeutic effect, such as an antibacterial or anticaries effect. Suitable levels of xylitol in dentifrice of the present invention are from about 0.01% to about 25%, preferably from about 3% to about 15%, more preferably from about 5% to about 12%, and most preferably from about 9% to about 1 1%, by weight of the composition.

Other Components

The dentifrice gels of the present invention can include a wide variety of optional components provided they are employed at levels which are not substantially detrimental to the clarity or stability of the gel. A non-exhaustive list includes:

Flavour Oil

The dentifrice of the present invention preferably comprises a flavour oil. The components of the flavour oil may be in the form of an oil, liquid, semi-solid, solid, or powder and may be of a natural and/or synthetic flavour origin. The term "flavour" according to the present invention means any essence, either natural or synthetic, or active agent (such as coolant agents), included in a composition to provide a palatable taste profile or physiological effect upon use. The flavour oil generally consists of a mixture of flavour components from the group consisting of peppermint, spearmint, cinnamon, spice, wintergreen, fruit, citrus, herbal, medicinal, and common food flavours (i.e. chocolate) and mixtures thereof Illustrative, but nonlimiting examples of such components include peppermint oils such as *Mentha piperita* and *Mentha arvensis*; spearmint oils such as *Mentha cardiaca* and *Mentha spicata*; hydrocarbons such as limonene, caryophyllene, myrcene, and humulene; alcohols such as menthol, linalool, 3-decanol, and pinocarveol; ketones such as piperitone, menthone, spicatone, and 1-carvone; aldehydes such as acetaldehyde, 3-hexanal, or n-octanal; oxides such as menthofuran, pepertione oxide, or carvyl acetate-7,7 oxide; acids such as acetic and ocenoic; and sulphides such as dimethyl sulphide. Components also include esters such as menthyl acetate, benzyl isobutyrate, and 3-octyl acetate. The esters are stable in compositions having a pH of about 7 or lower, and preferably a pH of about 4.5 or lower. The components can also include essential oils such as sage oil, parsley oil, mardoram oil, cassia oil, clove bud oil, cinnamon oil, eucalyptus oil, anise oil, and mixtures thereof The flavour components can also include chemicals such as cinnamic aldehyde, eugenol, ionone, anethole, eucalyptol, methyl salicylate, oxanone, alpha-irisone, vanillin, ethyl vanillin, heliotropine, propenyl guaethol, vanilla extracts, veratraldehyde, 4-cis-heptenal, diacetyl, butyl lactate, ethyl lactate, methyl-para-tert-butyl phenyl acetate, gamma and delta hexalactone and heptalactone, benzodihydropyrone, butter starter distillate, delta tetradecalactone, butyraldehyde, and mixtures thereof Preferred are peppermint oils, spearmint oils, menthol, anethole, methyl salicylate, cinnamon oils, clove bud oils, oxanone, and mixtures thereof Flavour components are described in more detail in Fenaroli's *Handbook of Flavour Ingredients*, Third Edition, Volumes 1 & 2, CRC Press, Inc. (1995), and Steffen Arctander's *Perfume and Flavour Chemicals*, Volumes 1 & 2, (1969). A physiological cooling agent may also be incorporated into the flavour oil. The coolant can be any of a wide variety of materials. Included among such materials are carboxamides, menthol, acetals, ketals, diols, and mixtures thereof Preferred coolants in the present compositions are the paramenthane carboxyamide agents such as N-ethyl-p-menthan-3-carboxamide, (known commercially as "WS-3") and mixtures thereof and methanone glycerine acetal (known commercially as "MGA"). Further disclosure of coolants suitable for the present invention are discussed in W097/06695, incorporated by reference herein. The flavour oil is used in the present composition at levels of from about 0.1% to about 10.0%, preferably from about 0.5% to about 5.0%, and most preferably from about 0.1% to about 2.0%, by weight of the composition.

Block Co-Polymer

Another optional component of the gels of the present invention is a block co-polymer.

Suitable block co-polymers have a HLB ("hydrophilic-lipophilic balance") within the range of greater than 5 and more preferably greater than 10, to less than 40, preferably less than 30 HLB. Suitable block co-polymers for the present invention are amine block co-polymers and polyoxyalkylene block co-polymers. Preferred are the polyoxyethylene-polyoxypropylene block co-polymers. Polyoxyethylene-polyoxypropylene block co-polymers are stable and readily dispersible in aqueous systems. These surfactants are often further defined in terms of the molecular weight of the polyoxypropylene hydrophobic moiety and the percent weight of the polyoxyethylene hydrophilic moiety. Liquid and low-melting poloxamers are commercially available from BASF under the Pluronic® tradename, ICI under the Synperonic tradename and Calgene under the Calgene Non-Ionic tradename. Preferred are those poloxamers containing from about 20% to about 90% ethylene oxide by weight, more preferred are those poloxamers containing from about 60% to 85% ethylene oxide by weight. Block co-polymers particularly useful herein are those which are soluble in water. Particularly preferred herein are those block co-polymers having a Ross Miles foam height (ASTM Method D-1173–53) measured in 0.1% aqueous solution at 26° C. of greater than 5 mm and more preferably greater than 10 mm.

When used, the dentifrice gels of the present invention comprise from about 0.1% to 10.0%, preferably from about 0.1% to about 4.0%, more preferably from about 0.2% to about 3.0% of a polyoxyethylene-polyoxypropylene block co-polymer.

Non-Ionic and Amphoteric Surfactants

Dentifrice of the present invention may also comprise non-ionic surfactants. Included amongst such non-ionic surfactants are substituted polyethylene glycol ethers selected from PEG-32 glyceryl stearate and PEG-40 sorbitan di-isostearate. Non-ionic surfactants can comprise from about 0.1% to 10.0%, preferably from about 0.1% to about 4.0%, more preferably from about 0.2% to about 3.0% by weight of the composition.

The compositions of the present invention can also optionally comprise an amphoteric surfactant. Amphoteric surfactants useful in the present invention can be broadly described as derivatives of aliphatic secondary and tertiary amines in which the aliphatic radical can be a straight chain or branched and wherein one of the aliphatic substituents contains from about 8 to about 18 carbon atoms and one contains an anionic water-solubilising group e.g. carboxylate, sulfonate, sulphate, phosphate or phosphonate. Other suitable amphoteric surfactants are betaines, specifically cocamidopropyl betaine. Mixtures of amphoteric surfactants may also be employed. Amphoteric surfactants or mixtures of anionic and amphoteric surfactants can be used at levels similar to those of anionic surfactants.

Fluoride Ion Source

A highly preferred component of the dentifrice of the present invention is a fluoride source capable of providing free fluoride ions. Preferred soluble fluoride ion sources include sodium fluoride, stannous fluoride, indium fluoride, and sodium monofluorophosphate. Sodium fluoride is the most preferred fluoride ion source. Norris et al., U.S. Pat. No. 2,946,725, issued Jul. 26, 1960, and Widder et al., U.S. Pat. No. 3,678,154 issued Jul. 18, 1972, disclose such fluoride ion sources as well as others.

The present compositions generally contain a fluoride source capable of providing from about 50 ppm to about 3500 ppm, and preferably from about 200 ppm to about 2500 ppm, more preferably from 500 ppm to 2000 ppm of free fluoride ions.

Colouring and Sweetening Agents

Colouring and sweetening agents may also be added.

The colouring agent may be in the form of an aqueous solution, preferably 1% colouring agent in a solution of water. Colour solutions generally comprise from about 0.01% to about 5%, by weight of the composition. An insoluble colouring agent such as a coloured speckle may also be used, provided it does not significantly obscure the overall, visually clear appearance of the gel. Pigmented silicas can be employed for this purpose, typically at a level of from 0.05 to 0.2%.

Suitable sweetening agents include sodium saccharin, dextrose, sucrose, chlorinated sucrose, lactose, maltose, levulose, aspartame, sodium cyclamate, D-tryptophan, dihydrochalcones, xylitol, acesulfame, monoammonium glycyrrhizinate, and mixtures thereof Sweetening agents are generally used in toothpastes at levels of from about 0.005% to about 5%, by weight of the composition.

Antimicrobial Agents

The gels of the present invention can also antimicrobial agents. Included among such agents are water insoluble non-cationic antimicrobial agents such as halogenated diphenyl ethers, phenolic compounds including phenol and its homologs, mono and poly-alkyl and aromatic halophenols, resorcinol and its derivatives, bisphenolic compounds and halogenated salicylanilides, benzoic esters, and halogenated carbanilides. The water soluble antimicrobials include quaternary ammonium salts and bis-biguanide salts, among others. Triclosan monophosphate is an additional water soluble antimicrobial agent. The quaternary ammonium agents include those in which one or two of the substitutes on the quaternary nitrogen has a carbon chain length (typically alkyl group) from about 8 to about 20, typically from about 10 to about 18 carbon atoms while the remaining substitutes (typically alkyl or benzyl group) have a lower number of carbon atoms, such as from about 1 to about 7 carbon atoms, typically methyl or ethyl groups. Dodecyl trimethyl ammonium bromide, tetradecylpyridinium chloride, domiphen bromide, N-tetradecyl-4-ethyl pyridinium chloride, dodecyl dimethyl (2-phenoxyethyl) ammonium bromide, benzyl dimethylstearyl ammonium chloride, cetyl pyridinium chloride, quaternized 5-amino-1, 3-bis(2-ethyl-hexyl)-5-methyl hexa hydropyrimidine, benzalkonium chloride, benzethonium chloride and methyl benzethonium chloride are exemplary of typical quaternary ammonium antibacterial agents. Preferably, when an anionic surfactant is used in the dentifrice of the present invention, a quaternary ammonium agent is not employed. Other compounds are bis[4-(R-amino)-1-pyridinium] alkanes as disclosed in U.S. Pat. No. 4,206,215, issued Jun. 3, 1980, to Bailey, incorporated herein by reference. Stannous salts such as stannous pyrophosphate and stannous gluconate and other antimicrobials such as copper bisglycinate, zinc citrate, and zinc lactate may also be included. Also useful are enzymes, including endoglycosidase, papain, dextranase, mutanase, and mixtures thereof Such agents are disclosed in U.S. Pat. No. 2,946,725, Jul. 26, 1960, to Norris et al. and in U.S. Pat. No. 4,051,234, Sep. 27, 1977 to Gieske et al., incorporated herein by reference. Specific antimicrobial agents include chlorhexidine, triclosan, triclosan monophosphate, and flavour oils such as thyrnol. Triclosan is particularly preferred. Triclosan and other agents of this type are disclosed in Parran, Jr. et al., U.S. Pat. No. 5,015,466, issued May 14, 1991, and U.S. Pat. No. 4,894,220, Jan. 16, 1990 to Nabi et al., incorporated herein by reference.

Binder

The present invention compositions in the form of toothpastes, typically contain some thickening material or binders to provide a desirable consistency. Thickening silicas have already been discussed. Other thickening agents useful in the present invention, either alone or in combination with the silicas, are carboxyvinyl polymers, carrageenan, hydroxyethyl cellulose, and water soluble salts of cellulose ethers such as sodium carboxymethylcellulose and sodium carboxymethyl hydroxyethyl cellulose. Natural gums such as gum karaya, xanthan gum, gum arabic, and gum tragacanth can also be used. These thickening agents can be used in an of amount from about 0.1% to about 15%, by weight of the composition.

Other suitable binders for the present invention include both synthetic and natural hectorites. A suitable synthetic hectorite for the present invention is sodium lithium magnesium silicates commercially available from Laporte, Southern Clay Co. under the Laponite® tradename (e.g CP, SP, D, SP2002). Natural hectorites suitable for the present invention include magnesium aluminium silicates such as Veegum which is commercially available from R. T. Vanderbilt and the montmorillonite clays which are commercially available from the Southern Clay Co. under the Gelwhite trade name, Bentone available from Rheox, Hectabrite available from American Colloid and Hectalite, also available from American Colloid. Bentonites are also suitable binders for the present invention. Preferred are the bentonites commercially available from Southern Clay Co. under the Bentolite trade name, Whittacker Clark and Danniels under the Bentonite trade name and American Colloid under the Palar Gel trade name. Fumed or colloidal silica are further suitable binders for the present invention. When the binder of the dentifrice is a hectorite, bentonite or fumed silica as described herein, it is generally present at a level of from about 0.1% to about 10% by weight of the composition.

Peroxide Source

The dentifrice of the present invention can also include a peroxide source. The peroxide source is suitably selected from hydrogen peroxide, calcium peroxide, urea peroxide, and mixtures thereof The preferred peroxide source is calcium peroxide. The following amounts represent the amount of peroxide raw material, although the peroxide source may contain ingredients other than the peroxide raw material. The present composition may contain from about 0.01% to about 10%, preferably from about 0.1% to about 5%, more preferably from about 0.2% to about 3%, and most preferably from about.0.3% to about 0.8% of a peroxide source, by weight of the composition.

Alkali Metal Bicarbonate Salt

The present invention may also include an alkali metal bicarbonate salt. Alkali metal bicarbonate salts are soluble in water and, unless stabilised, tend to release carbon dioxide in an aqueous system. Sodium bicarbonate, also known as baking soda, is the preferred alkali metal bicarbonate salt. The present composition may contain up to 10%, preferably from about 0.5% to about 5%, more preferably from about 0.1% to about 1%.

Alkalis and Buffers

The pH of the present compositions is preferably adjusted through the use of buffering agents. Buffering agents, as used herein, refer to agents that can be used to adjust the pH of the compositions to a preferred range of about pH 7.5 to about pH 10, more preferably from about pH 8 to about pH 9.5. These agents include monosodium phosphate, trisodium phosphate, sodium hydroxide, sodium carbonate, citric acid, and sodium citrate. Buffering agents can be used at a level of from about 0.01% to about 10%, by weight of the present compositions.

The dentifrice of the present invention may also additionally comprise a short chain, saturated, hydrocarbon alcohol, wherein the short chain alcohol is selected from ethanol, propanol or butanol. Preferred is ethanol. When used, the short chain alcohol is generally present at levels of from about 1% to about 10%.

If desired, air may be incorporated into the dentifrice of the present invention such that the density of the unaerated dentifrice is reduced by up to 25%.

EXAMPLES

The following examples further describe and demonstrate embodiments within the scope of the present invention. For all examples, the ingredients are mixed under partial vacuum.

Examples A to F are anticalculus products of high clarity which have a pH in the range from 8.4 to 8.7. They are prepared as follows. The glycerin/propylene glycol/xanthan gum/CMC (where used), are mixed in a vessel to form a suspension. The sorbitol solution, water, sodium fluoride, sodium saccharin and sodium hydroxide (32%) or sodium carbonate are added to the vessel and mixed until homogenous. The silicas and other water insoluble inorganics are pre-mixed and added into the vessel. Mixing is continued until homogenous. A premix of the triclosan, PEG, flavour and sodium alkyl sulphate solution is formed separately and added to the contents of the main vessel. Lastly, the anhydrous tetrasodium pyrophosphate is added to the vessel and the contents mixed until homogenous.

What is claimed is:

1. A visually clear, dentifrice gel comprising
   a) sufficient tetasodium pyrophosphate to provide from about 0.2% to about 5% pyrophosphate anion;
   b) a silica dental abrasive having a refractive index of from 1.445 to 1.47;
   c) from about 0–7% to about 3% sodium alkyl sulphate; and
   d) an aqueous liquid carrier, wherein the gel comprises less than about 25% total water and has a neat pH of from 8 to 10 and a RDA of from 50 to 200.

2. A gel, according to claim 1, comprising sorbitol as a primary humectant and a secondary humectant selected from glycerin, propylene glycol, polyethylene glycols of MW less than 1500 and mixtures thereof.

3. A process for making a gel according to claim 1 comprising the step of adding anhydrous tetrasodium pyrophosphate to the aqueous carrier.

4. A process according to claim 3 wherein the anhydrous tetrasodium pyrophosphate is added after the addition of any thickening agents.

5. A process for making a visually clear, dentifrice gel comprising the step of adding anhydrous tetrasodium pyrophosphate to an aqueous carrier, the gel comprising
   a) a silica dental abrasive having a refractive index of from 1.445 to 1.47; and
   b) an aqueous liquid carrier comprising less than 27% total water.

6. A gel according to claim 1, which has a neat pH of from 8 to 9.5.

* * * * *

UNITED STATES PATENT AND TRADEMARK OFFICE
CERTIFICATE OF CORRECTION

PATENT NO.    : 6,479,038 B1
DATED         : November 12, 2002
INVENTOR(S)   : Trevor Neil Day It is certified that error appears in the above-identified patent and that said Letters Patent is hereby corrected as shown below:

Column 57,
Line 7, delete "efficiency" and insert -- efficacy --

Signed and Sealed this

Ninth Day of December, 2003

JAMES E. ROGAN
*Director of the United States Patent and Trademark Office*